(12) United States Patent
Henry, Jr. et al.

(10) Patent No.: US 11,812,790 B2
(45) Date of Patent: *Nov. 14, 2023

(54) USER INTERFACE FOR AN AEROSOL DELIVERY DEVICE

(71) Applicant: R.J. Reynolds Tobacco Company, Winston-Salem, NC (US)

(72) Inventors: Raymond Charles Henry, Jr., Cary, NC (US); Glen Joseph Kimsey, Cary, NC (US); Frederic Philippe Ampolini, Winston-Salem, NC (US); James William Rogers, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/940,814

(22) Filed: Sep. 8, 2022

(65) Prior Publication Data

US 2023/0000173 A1     Jan. 5, 2023

Related U.S. Application Data

(63) Continuation of application No. 16/928,115, filed on Jul. 14, 2020, now Pat. No. 11,464,259, which is a
(Continued)

(51) Int. Cl.
*A24F 40/60* (2020.01)
*A61M 15/00* (2006.01)
(Continued)

(52) U.S. Cl.
CPC .............. *A24F 40/60* (2020.01); *A24F 40/65* (2020.01); *A61M 15/00* (2013.01); *A24F 40/10* (2020.01)

(58) Field of Classification Search
CPC ........ A24F 47/008; A24F 40/10; A24F 40/60; A24F 40/65; A61M 15/00
See application file for complete search history.

(56) References Cited

U.S. PATENT DOCUMENTS

| 1,771,366 A | 7/1930 | Wyss |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

*Primary Examiner* — Shogo Sasaki
(74) *Attorney, Agent, or Firm* — Womble Bond Dickinson (US) LLP

(57) ABSTRACT

An aerosol delivery device is provided that includes a user interface including a pushbutton and a display. A control component contained coupled to the user interface controls operation of at least one functional element of the aerosol delivery device. The control component controls the display to present a menu including a plurality of menu items selectable using only the pushbutton. Each menu item of the plurality of menu items is associated with a respective functional element of the aerosol delivery device, and the control component is configured to navigate the plurality of menu items, and select a currently-presented menu item of the plurality of menu items for control of the respective functional element, in response to respective first and second types of presses of the pushbutton, the first and second types of presses being of different durations.

20 Claims, 16 Drawing Sheets

Related U.S. Application Data continuation of application No. 16/233,402, filed on Dec. 27, 2018, now Pat. No. 10,729,185, which is a continuation of application No. 14/930,136, filed on Nov. 2, 2015, now Pat. No. 10,201,187.

(51) Int. Cl.
*A24F 40/65* (2020.01)
*A24F 40/10* (2020.01)

(56) References Cited

U.S. PATENT DOCUMENTS

| | | |
|---|---|---|
| 2,104,266 A | 1/1938 | Mccormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols et al. |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0150451 A1* | 8/2003 | Shayan .............. A24F 47/008 128/203.12 |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Llewellyn Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Han |
| 2009/0095312 A1 | 4/2009 | Herbrich et al. |
| 2009/0126745 A1 | 5/2009 | Hon |
| 2009/0188490 A1 | 7/2009 | Han |
| 2009/0230117 A1 | 9/2009 | Fernando et al. |
| 2009/0237247 A1* | 9/2009 | Brunetti .............. G08B 13/196 340/541 |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0007139 A1* | 1/2011 | Brunetti .......... G08B 13/19613 348/51 |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0048266 A1 | 3/2012 | Alelov |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0042865 A1* | 2/2013 | Monsees .............. A61M 15/06 128/203.27 |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0306084 A1 | 11/2013 | Flick |

(56) References Cited

U.S. PATENT DOCUMENTS

| | | | |
|---|---|---|---|
| 2013/0312742 A1* | 11/2013 | Monsees | A61M 15/06 128/202.21 |
| 2013/0319439 A1 | 12/2013 | Gorelick et al. | |
| 2013/0340750 A1 | 12/2013 | Thorens et al. | |
| 2013/0340775 A1 | 12/2013 | Juster et al. | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |
| 2014/0109921 A1 | 4/2014 | Chen | |
| 2014/0157583 A1 | 6/2014 | Ward et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2014/0334804 A1* | 11/2014 | Choi | A61M 15/06 392/404 |
| 2014/0345631 A1 | 11/2014 | Bowen et al. | |
| 2014/0366898 A1* | 12/2014 | Monsees | A24F 47/008 131/329 |
| 2015/0053217 A1* | 2/2015 | Steingraber | A24F 47/008 131/329 |
| 2016/0262459 A1* | 9/2016 | Monsees | A61M 11/042 |
| 2016/0338412 A1* | 11/2016 | Monsees | A24F 47/008 |
| 2017/0020198 A1* | 1/2017 | Naqwi | G01M 99/008 |
| 2018/0146709 A1* | 5/2018 | Bessant | A24F 47/008 |

FOREIGN PATENT DOCUMENTS

| | | |
|---|---|---|
| CN | 1541577 | 11/2004 |
| CN | 2719043 | 8/2005 |
| CN | 1782977 | 6/2006 |
| CN | 200997909 | 1/2008 |
| CN | 101116542 | 2/2008 |
| CN | 101176805 | 5/2008 |
| CN | 201379072 | 1/2010 |
| CN | 202999297 | 6/2013 |
| CN | 103783675 | 5/2014 |
| CN | 203952416 | 11/2014 |
| CN | 203986117 U | 12/2014 |
| CN | 104323429 | 2/2015 |
| CN | 104432537 | 3/2015 |
| CN | 204466899 | 7/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | O 430 566 | 6/1991 |
| EP | O 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO2010/003480 | 1/2010 |
| WO | WO2010/045670 | 4/2010 |
| WO | WO2010/073122 | 7/2010 |
| WO | WO2010/118644 | 10/2010 |
| WO | WO2010/140937 | 12/2010 |
| WO | WO2011/010334 | 1/2011 |
| WO | WO2012/072762 | 6/2012 |
| WO | WO 2012/100523 | 8/2012 |
| WO | WO2013/089551 | 6/2013 |
| WO | 2013098398 A2 | 7/2013 |
| WO | WO 2014/066730 | 5/2014 |

\* cited by examiner

USER INTERFACE FOR AN AEROSOL DELIVERY DEVICE

CROSS-REFERENCE TO RELATED APPLICATION(S)

This application is a continuation of U.S. patent application Ser. No. 16/928,115, filed Jul. 14, 2020, now U.S. Pat. No. 11,464,259, which is a continuation of U.S. patent application Ser. No. 16/233,402, filed Dec. 27, 2018, now U.S. Pat. No. 10,729,185, which is a continuation of U.S. patent application Ser. No. 14/930,136, filed Nov. 2, 2015, now U.S. Pat. No. 10,201,187, all of which are hereby incorporated by reference in their entirety.

TECHNOLOGICAL FIELD

The present disclosure relates to aerosol delivery devices such as smoking articles that may utilize electrically generated heat for the production of aerosol (e.g., smoking articles commonly referred to as electronic cigarettes), and more particularly to a user interface integrated within an aerosol delivery device. The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference.

Ongoing developments in the field of aerosol delivery devices have resulted in increasingly sophisticated aerosol delivery devices. For example, some aerosol delivery devices utilize user interfaces (e.g., a pushbutton, a display, and the like) to facilitate user interaction with the aerosol delivery device. However, the user interfaces, as currently configured, provide limited control of functions for the aerosol delivery device. Therefore, a need exist for a user interface that provides comprehensive options for controlling functions of an aerosol delivery device and further simplifies user interaction with the aerosol delivery device.

BRIEF SUMMARY

The present disclosure relates to aerosol delivery devices, methods of forming such devices, and elements of such devices. The present disclosure thus includes, without limitation, the following example implementations. In some example implementations, an aerosol delivery device is provided that includes at least one housing, a user interface including a pushbutton and a display on the at least one housing, and a control component. The control component may be contained within the at least one housing and coupled to the user interface. The control component may be configured to control operation of at least one functional element of the aerosol delivery device in response to detection of airflow through at least a portion of the at least one housing.

The control component may be further configured to control the display to present a menu including a plurality of menu items selectable using only a single pushbutton. Each menu item of the plurality of menu items may be associated with a respective functional element of the aerosol delivery device. The control component may be configured to navigate the plurality of menu items, and select a currently-presented menu item of the plurality of menu items for control of the respective functional element, in response to respective first and second types of presses of the pushbutton, the first and second types of presses being of different durations.

In some example implementations of the aerosol delivery device of the preceding or any subsequent example implementation, or any combination thereof, the duration of the second type of press of the pushbutton is substantially longer than the duration of the first type of press of the pushbutton, and the control component being configured to select the currently-presented menu item includes being configured to control the display to present a progress bar to visually indicate progression of a press of the pushbutton up to the duration of the second type of press of the pushbutton.

In some example implementations of the aerosol delivery device of any preceding or any subsequent example implementation, or any combination thereof, the control component being configured to control the display to present the progress bar includes being configured to automatically update the progress bar with progression of the press of the pushbutton, and reset the progress bar in at least one instance in which the pushbutton is released before the duration of the second type of press.

In some example implementations of the aerosol delivery device of any preceding or any subsequent example implementation, or any combination thereof, in at least one instance, the respective functional element with which the currently-presented menu item is associated is a power source of the aerosol delivery device, and selection of the currently-presented menu item causes the aerosol delivery device to power off.

In some example implementations of the aerosol delivery device of any preceding or any subsequent example implementation, or any combination thereof, the aerosol delivery device of further comprises a heating element controllable by the control component to activate and vaporize components of an aerosol precursor composition in response to the detection of airflow, the airflow being combinable with a thereby formed vapor to form an aerosol. In which, in at least one instance, the respective functional element with which the currently-presented menu item is associated is the heating element, and the control component is configured to effect an alteration of a power level of the heating element, and control the display to present a confirmation of the alteration, in response to selection of the currently-presented menu item.

In some example implementations of the aerosol delivery device of any preceding or any subsequent example implementation, or any combination thereof, in at least one instance, the respective functional element with which the currently-presented menu item is associated is a Bluetooth communication interface, and the control component is configured to effect a reset of the Bluetooth communication interface, and control the display to present a confirmation of the reset, in response to selection of the currently-presented menu item.

In some example implementations of the aerosol delivery device of any preceding or any subsequent example implementation, or any combination thereof, in at least one instance, the respective functional element with which the currently-presented menu item is associated is the display, and the presently-presented menu item is further associated with an audio component. In which, in the at least one instance, the control component is configured to effect a dimming of the display and a muting of the audio component, and control the display to present a confirmation of the dimming and muting, in response to selection of the currently-presented menu item.

In some example implementations of the aerosol delivery device of any preceding or any subsequent example implementation, or any combination thereof, in at least one instance, the respective functional element with which the currently-presented menu item is associated is a power source, and a cartridge containing an aerosol precursor composition. In which, the control component being configured to navigate the plurality of menu items includes being configured to control the display to present a current power level of the power source and a current level of the aerosol precursor composition within the cartridge.

In some example implementations of the aerosol delivery device of any preceding or any subsequent example implementation, or any combination thereof, the control component is further configured to turn off the display after a predetermined period of time has elapsed without a press of the pushbutton of either the first type or second type.

In some example implementations of the aerosol delivery device of any preceding or any subsequent example implementation, or any combination thereof, the control component is configured to detect an alert event associated with the aerosol delivery device, and in response to a separate display trigger, control the display to present an alert corresponding thereto. The separate display trigger may include at least one of the detection of airflow through at least a portion of the at least one housing, first and second types of presses of the pushbutton, or connection of the aerosol delivery device to a charging component.

In some example implementations, a method for controlling operation of an aerosol delivery device including at least at least one housing containing a user interface including a pushbutton and a display on the at least one housing, and a control component contained within the at least one housing and coupled to the user interface. The method may include controlling operation of at least one functional element of the aerosol delivery device in response to detection of airflow through at least a portion of the at least one housing. The method may also include controlling the display to present a menu including a plurality of menu items selectable using only the pushbutton. Each menu item of the plurality of menu items may be associated with a respective functional element of the aerosol delivery device. The method may also include navigating the plurality of menu items, and selecting a currently-presented menu item of the plurality of menu items for control of the respective functional element, in response to respective first and second types of presses of the pushbutton, the first and second types of presses being of different durations.

In some example implementations of the method of the preceding or any subsequent example implementation, or any combination thereof, the duration of the second type of press of the pushbutton is substantially longer than the duration of the first type of press of the pushbutton, and controlling the display to present the menu includes controlling the display to present a progress bar associated with the currently-presented menu item and configured to visually indicate progression of a press of the pushbutton up to the duration of the second type of press of the pushbutton. In which, selecting the currently-presented menu item includes controlling the display to present a progress bar to visually indicate progression of a press of the pushbutton up to the duration of the second type of press of the pushbutton.

In some example implementations of the method of any preceding or any subsequent example implementation, or any combination thereof, controlling the display to present the progress bar includes automatically updating the progress bar with progression of the press of the pushbutton, and resetting the progress in at least one instance in which the pushbutton is released before the duration of the second type of press.

In some example implementations of the method of any preceding or any subsequent example implementation, or any combination thereof, in at least one instance, the respective functional element with which the currently-presented menu item is associated is a power source of the aerosol delivery device, and selection of the currently-presented menu item causes the aerosol delivery device to power off.

In some example implementations of the method of any preceding or any subsequent example implementation, or any combination thereof, the aerosol delivery device further includes a heating element controllable by the control component. In which, in at least one instance, the respective functional element with which the currently-presented menu item is associated is the heating element, and the method further comprises activating the heating element to vaporize components of an aerosol precursor composition in response to the detection of airflow, the airflow being combinable with a thereby formed vapor to form an aerosol, effecting an alteration of a power level of the heating element, and controlling the display to present a confirmation of the alteration, in response to selection of the currently-presented menu item.

In some example implementations of the method of any preceding or any subsequent example implementation, or any combination thereof, in at least one instance, the respective functional element with which the currently-presented menu item is associated is a Bluetooth communication interface, and the method further comprises effecting a reset of the Bluetooth communication interface, and controlling the display to present a confirmation of the reset, in response to selection of the currently-presented menu item.

In some example implementations of the method of any preceding or any subsequent example implementation, or any combination thereof, in at least one instance, the respective functional element with which the currently-presented menu item is associated is the display, and the presently-presented menu item is further associated with an audio component. In which, in the at least one instance, the method further comprises effecting a dimming of the display and a muting of the audio component, and controlling the display to present a confirmation of the dimming and muting, in response to selection of the currently-presented menu item.

In some example implementations of the method of any preceding or any subsequent example implementation, or any combination thereof, in at least one instance, the respective functional element with which the currently-presented menu item is associated is a power source, and a cartridge containing an aerosol precursor composition. In which, navigating the plurality of menu items includes controlling the display to present a current power level of the power source and a current level of the aerosol precursor composition within the cartridge.

In some example implementations of the method of any preceding or any subsequent example implementation, or any combination thereof, the method further comprises at the control component turning off the display after a predetermined period of time has elapsed without a press of the pushbutton of either the first type or second type.

In some example implementations of the method of any preceding or any subsequent example implementation, or any combination thereof, the method further comprises detecting an alert event associated with the aerosol delivery device; and in response to a separate display trigger, controlling the display to present an alert corresponding thereto, the separate display trigger including at least one of the detection of airflow through at least a portion of the at least one housing, first and second types of presses of the pushbutton, or the connection of the aerosol delivery device to a charging component.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Figure 1:
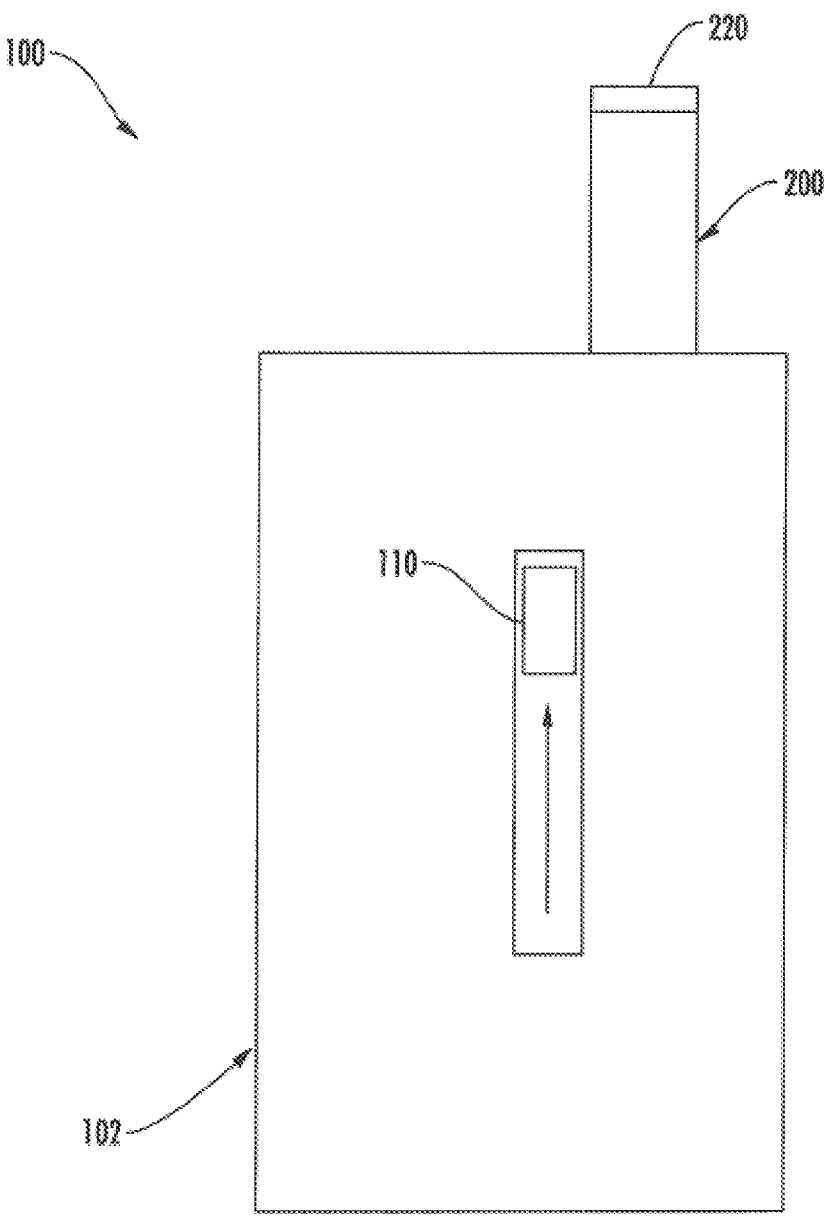
Figure 2:
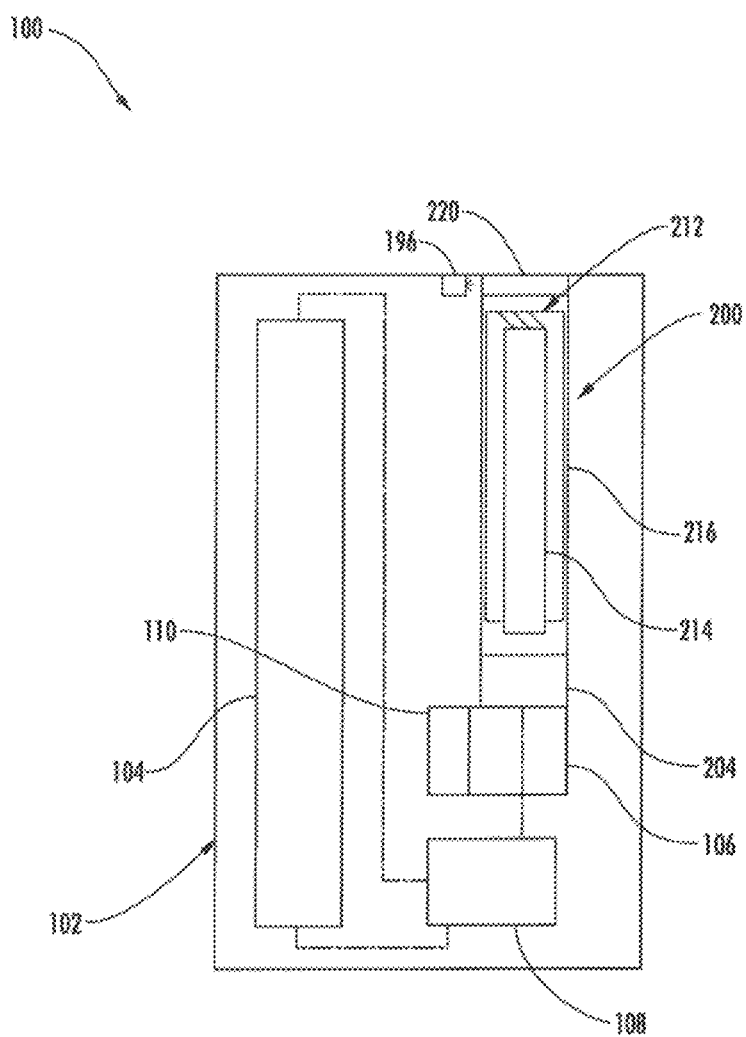
Figure 3:
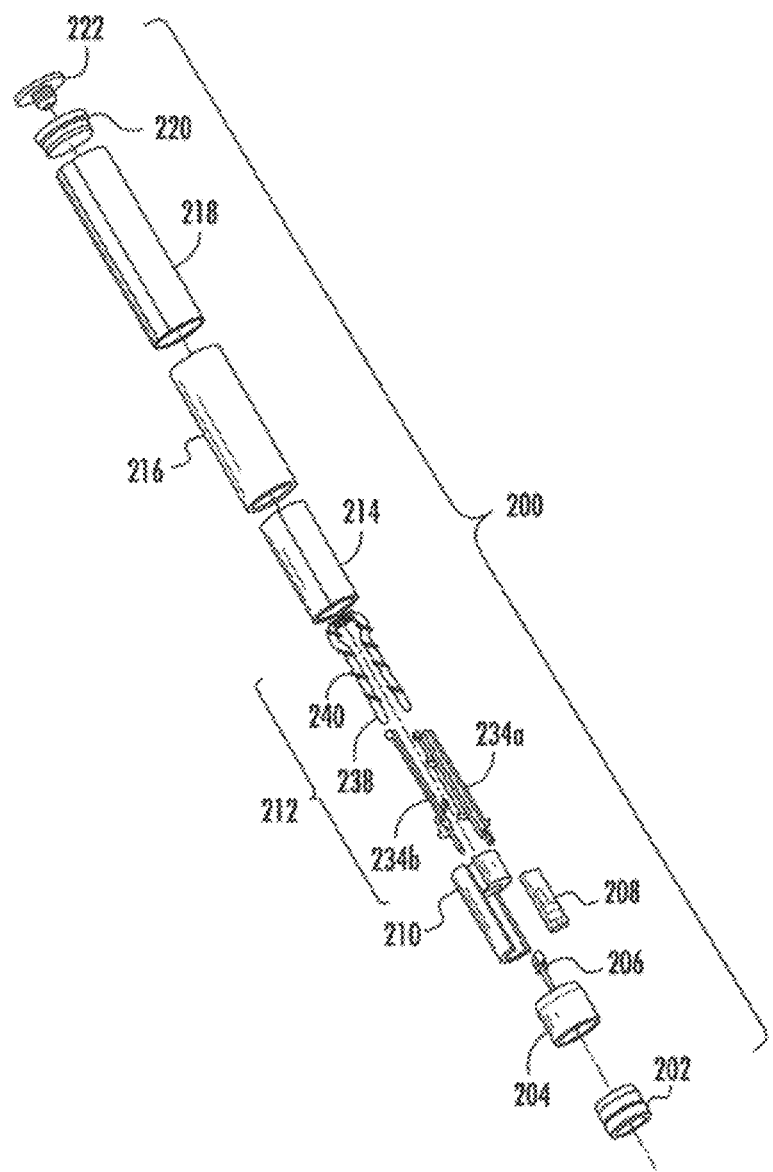
Figure 4:
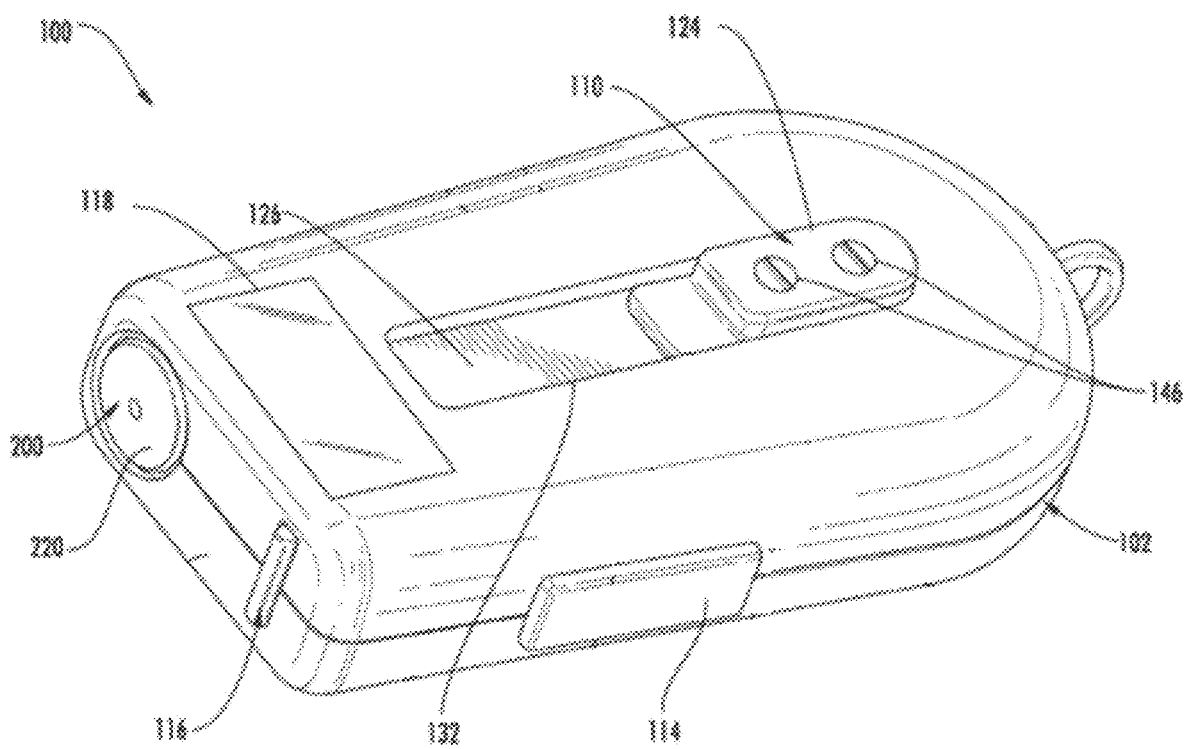
Figure 5:
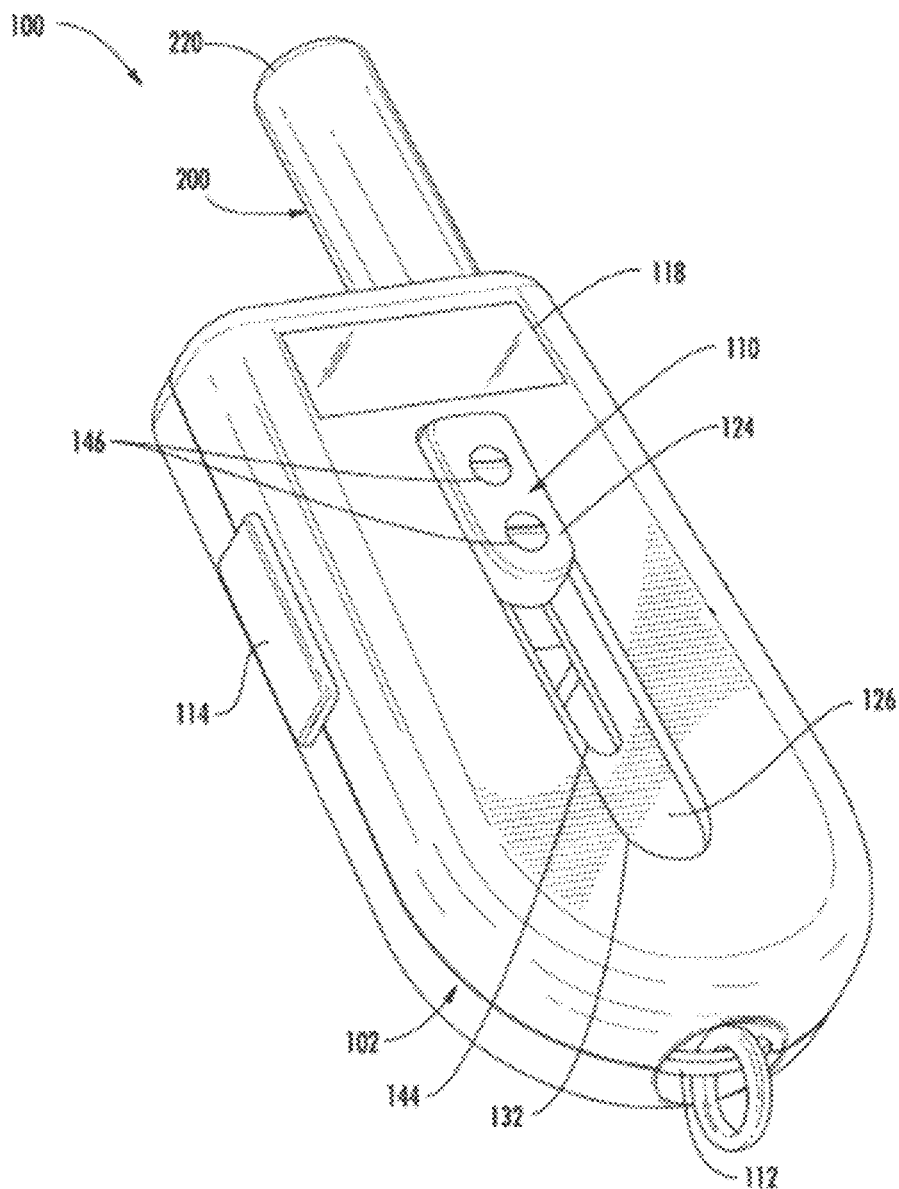
Figure 6:
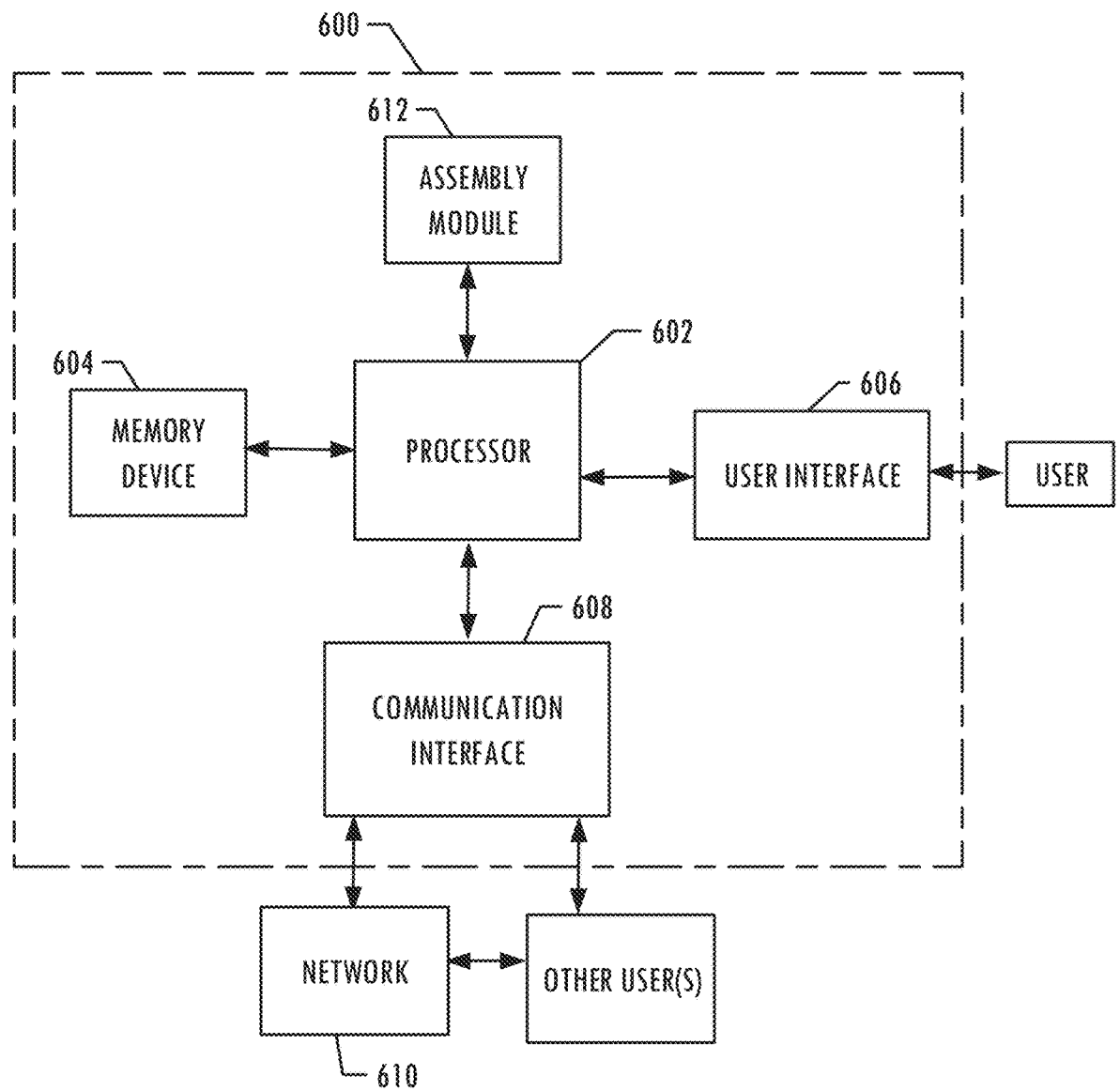
Figure 15:
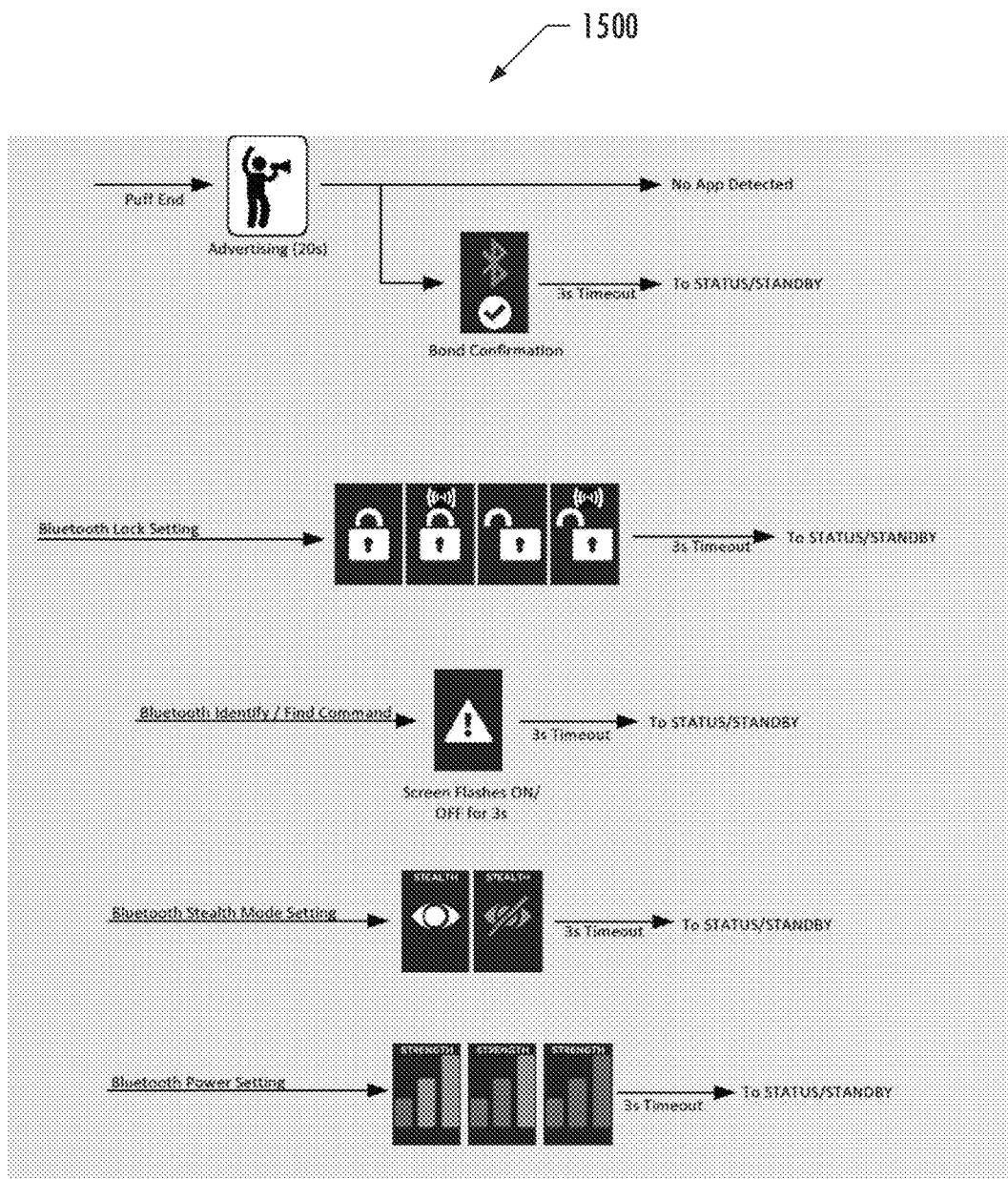
Figure 16:
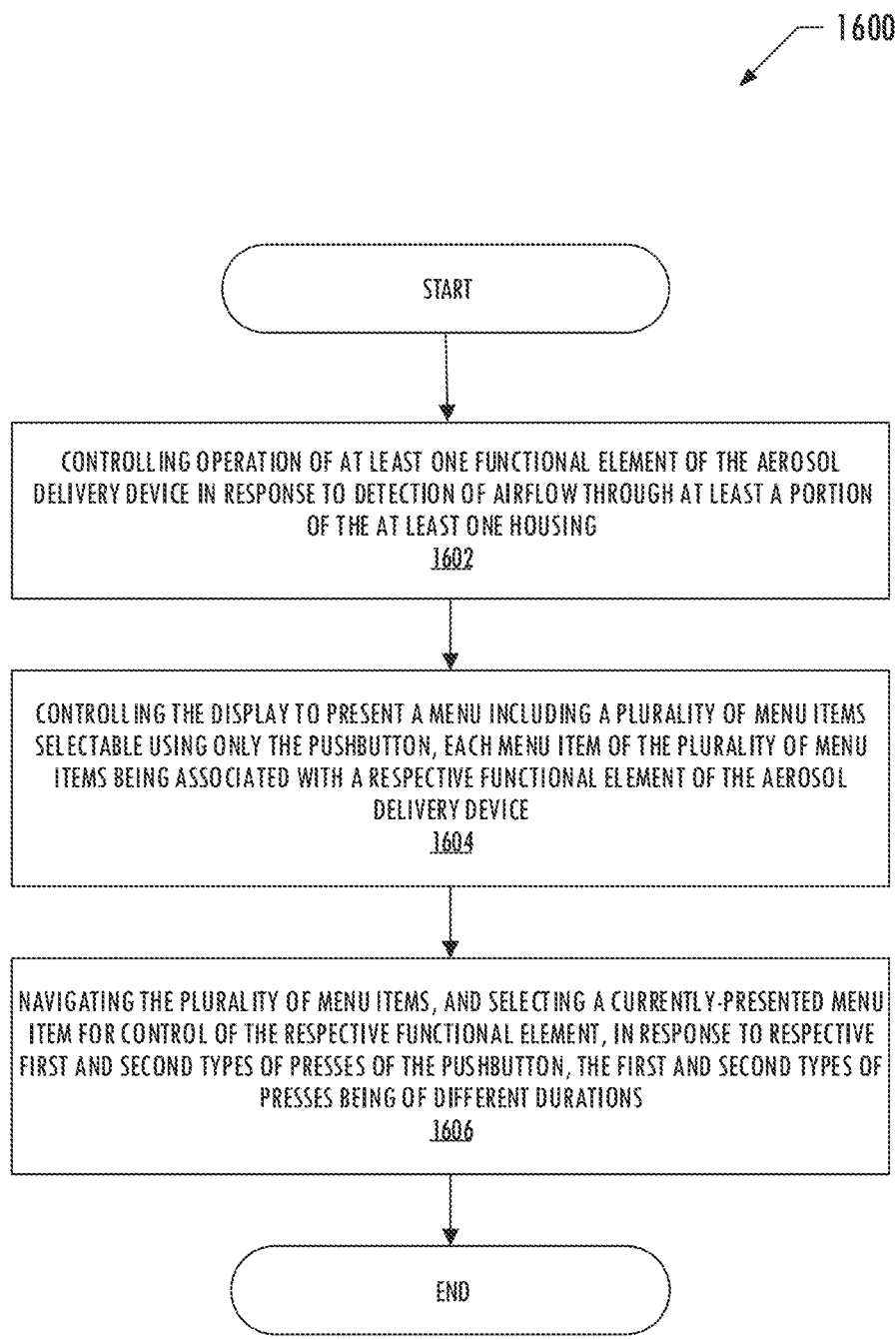

Having thus described the disclosure in the foregoing general terms, reference will now be made to the accompanying drawings, which are not necessarily drawn to scale, and wherein:

FIG. 1 illustrates a front view of an aerosol delivery device including a housing having a cartridge therein, according to an example implementation of the present disclosure;

FIG. 2 schematically illustrates a sectional view through the aerosol delivery device of FIG. 1, according to an example implementation of the present disclosure;

FIG. 3 illustrates an exploded view of a cartridge suitable for use in the aerosol delivery device of FIG. 1, according to an example implementation of the present disclosure;

FIG. 4 illustrates a perspective view of the aerosol delivery device of FIG. 1, according to an example implementation of the present disclosure;

FIG. 5 illustrates an opposing perspective view of the aerosol delivery device of FIG. 1, according to an example implementation of the present disclosure;

FIG. 6 illustrates a control component according to an example implementation of the present disclosure;

FIGS. 7-15 illustrate various functions of an aerosol delivery device user interface, according to some example implementations; and FIG. 16 illustrates various operations in a method of providing an aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Aerosol delivery devices are often configured in a manner that mimics aspects of certain traditional smoking devices such as cigarettes or cigars. In this regard, aerosol delivery devices typically define a substantially cylindrical configuration. Typically, an elongated body resembling the shape of a cigarette or cigar can be formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. Aerosol delivery devices often include a control body and a cartridge which attach in an end-to-end relationship to define the substantially cylindrical configuration.

While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, the cylindrical configuration may result in the mouthpiece being exposed to the surrounding environment and therefore susceptible to contamination. Accordingly, it may be desirable to provide aerosol delivery devices in configurations that differ from shapes associated with traditional smoking articles.

In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and integral with or removably coupled thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller component), a heating element or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined airflow path through the article such that aerosol generated can be withdrawn therefrom upon draw).

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate). A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

In some implementations, the aerosol delivery device can include an indicator, which may comprise one or more light emitting diodes or a graphical user interface via a display. The indicator can be in communication with the control component through a connector circuit and illuminate, for example, during a user draw on the mouthend as detected by the flow sensor.

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

FIG. 1 illustrates a front view of an aerosol delivery device 100, and FIG. 2 illustrates a modified sectional view through the aerosol delivery device, according to an example implementation of the present disclosure. As illustrated, the aerosol delivery device 100 may comprise a housing 102 and a cartridge 200. The cartridge may be moveable with respect to at least a portion of, or an entirety of, the housing. In particular, the cartridge may be moveable relative to at least a portion of the housing between an extended configuration illustrated in FIG. 1, and a retracted configuration illustrated in FIG. 2. Details with respect to the mechanisms and manners associated with movement of the cartridge relative to the housing are described hereinafter.

In some example implementations, one or both of the housing 102 and the cartridge 200 of the aerosol delivery device 100 may be referred to as being disposable or as being reusable. The aerosol delivery device may include various other components disposed within the housing 102 or the cartridge 200 or otherwise coupled thereto. These components may be distributed between the housing and the cartridge in any of various manners. For example, the housing may include a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. Further, in some example implementations, the cartridge may comprise a single-use cartridge, as disclosed in U.S. Pat. No. 8,910,639 to Chang et al., which is incorporated herein by reference in its entirety. Accordingly, it should be understood that the described implementations are provided for example purposes only.

In one example implementation, the housing 102 and cartridge 200 forming the aerosol delivery device 100 may be permanently coupled to one another. Examples of aerosol delivery devices that may be configured to be disposable and/or which may include first and second outer bodies that are configured for permanent coupling are disclosed in U.S. patent application Ser. No. 14/170,838 to Bless et al., filed Feb. 3, 2014, which is incorporated herein by reference in its entirety. In another example implementation, the cartridge and control body may be configured in a single-piece, non-detachable form and may incorporate the components, aspects, and features disclosed herein. However, in another example implementation, the control body and cartridge may be configured to be separable such that, for example, the cartridge may be refilled or replaced.

By way of example, in the illustrated implementation of FIG. 2, the aerosol delivery device 100 includes a power source 104 (e.g., a battery) positioned within the housing 102. Further, a connector 106 may be moveably attached to the housing. The cartridge 200 may be engaged with the connector so as to be moveable relative to at least a portion of the housing. In some implementations, the cartridge may be removably engaged with the connector and replaceable.

The aerosol delivery device 100 may additionally include a control component 108 received therein. The control component may be configured to direct electrical power from the power source 104 to the cartridge 200 to heat the aerosol precursor composition retained in the reservoir 214 with the atomizer 212 to produce a vapor, which may occur during a user draw on the mouthpiece 220 of the cartridge. The control component includes a number of electronic components, and in some examples may be formed of a printed circuit board (PCB) that supports and electrically connects the electronic components. Examples of suitable electronic components include a microprocessor or processor core, an integrated circuit (IC), a memory, and the like. In some examples, the control component may include a microcontroller with an integrated processor core and memory, and which may further include one or more integrated input/output peripherals.

As noted above, the cartridge 200 may be moveable relative to the housing 102. In this regard, the aerosol delivery device 100 may further comprise an actuator 110. In particular, the actuator may be coupled to the connector 106. Thereby, the actuator may be operatively engaged with the cartridge and configured to move the cartridge between the extended configuration and the retracted configuration.

As illustrated in FIG. 1, the mouthpiece 220 may be exposed when the cartridge 200 is in the extended configuration. In other words the mouthpiece may be positioned outside of the housing 102 when the cartridge is in the extended configuration such that a user may engage the mouthpiece with his or her lips. Thus, the extended configuration of the cartridge is a configuration in which the aerosol delivery device 100 is configured to receive a draw on the mouthpiece 220 such that the aerosol delivery device may produce and deliver an aerosol to a user in the manner described above.

Conversely, as illustrated in FIG. 2, in the retracted configuration the mouthpiece 220 is relatively closer to the housing 102 than in the extended configuration of FIG. 1. In the retracted configuration, the mouthpiece may be flush with respect to the housing. In other words, an outer surface of the mouthpiece may substantially align with an outer surface of the housing. In another implementation the mouthpiece may be recessed with respect to the housing. In other words, a gap may be provided between the outer surface of the mouthpiece and the outer surface of the housing.

FIG. 3 illustrates a more particular example of the cartridge 200 of FIGS. 1 and 2. As illustrated, the cartridge may comprise a base shipping plug 202, a base 204, a control component terminal 206, an electronic control component 208, a flow tube 210, an atomizer 212, a reservoir 214, an outer body 216, a label 218, a mouthpiece 220, and a mouthpiece shipping plug 222 according to an example implementation of the present disclosure.

The base 204 may be coupled to a first end of the outer body 216 and the mouthpiece 220 may be coupled to an opposing second end of the outer body to at least partially enclose the remaining components of the cartridge 200 therein, with the exception of the label 218, the mouthpiece shipping plug 222, and the base shipping plug 202. The base may be configured to engage an associated device including a power source 104. In some implementations, the base may comprise anti-rotation features that substantially prevent relative rotation between the cartridge and associated device including the power source. The base shipping plug may be configured to engage and protect the base prior to use of the cartridge. Similarly, the mouthpiece shipping plug may be configured to engage and protect the mouthpiece prior to use of the cartridge.

The control component terminal 206, the electronic control component 208, the flow tube 210, the atomizer 212, and the reservoir substrate 214 may be retained within the outer body 216. The label 218 may at least partially surround the outer body and include information such as a product identifier thereon. The atomizer 212 may comprise a first heating terminal 234a and a second heating terminal 234b, a liquid transport element 238 and a heating element 240.

In some example, a valve may be positioned between the reservoir and the heating element, and configured to control an amount of aerosol precursor composition passed or delivered from the reservoir to the heating element.

The reservoir 214 may be a container or can be a fibrous reservoir, as presently described. For example, the reservoir may comprise one or more layers of nonwoven fibers substantially formed into the shape of a tube encircling the interior of the cartridge 200. An aerosol precursor composition can be retained in the reservoir. Liquid components, for example, can be sorptively retained by the reservoir. The reservoir can be in fluid connection with the liquid transport element 238 adapted to wick or otherwise transport an aerosol precursor composition stored in the reservoir housing to the heating element 240. In particular, the liquid transport element can transport the aerosol precursor composition stored in the reservoir via capillary action to the heating element that is in the form of a metal wire coil in this example. As such, the heating element is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 3 as described herein. In particular, specific combinations of heating members and transport elements as further described below may be incorporated into devices such as illustrated in FIG. 3 as described herein.

Various examples of materials configured to produce heat when electrical current is applied therethrough may be employed to form the heating element 240. The heating element in these examples may be resistive heating element such as a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum (Mo(Si,Al)$_2$), graphite and graphite-based materials (e.g., carbon-based foams and yarns) and ceramics (e.g., positive or negative temperature coefficient ceramics). Example implementations of heating elements or heating members useful in aerosol delivery devices according to the present disclosure are further described below, and can be incorporated into devices such as illustrated in FIG. 3 as described herein.

The cartridge 200 may include a flow director defining a non-tubular configuration, an electronics compartment sealed with respect to a reservoir compartment, and/or any of the various other features and components disclosed therein. Accordingly, it should be understood that the particular implementation of the cartridge described herein is provided for example purposes only. In this regard, the cartridge is schematically illustrated in FIG. 2 as including only the outer body 216, the mouthpiece 220, the atomizer 212, the reservoir 214, and the base 204, in light of the various alternate and additional components that may be included therein.

One or more components of the cartridge 200 may be configured to form an electrical connection with the connector 106. For example, referring to the cartridge implementation of FIG. 3, the first heating terminal 234a and the second heating terminal 234b (e.g., positive and negative terminals) at the opposing ends of the heating element 240 are configured to form an electrical connection with the connector. Further, the electronic control component 208 (see FIG. 3) may form an electrical connection with the connector through the control component terminal 206 (see FIG. 3). Components within the housing 102 (e.g., the control component 108) may thus employ the electronic control component to determine whether the cartridge is genuine and/or perform other functions. However, in other implementations the connection between the connector and the cartridge may not be electrical. In other words, the connection between the connector and the cartridge may be purely mechanical. In these implementations, atomization may occur outside of the cartridge or atomization may occur via other methods not requiring electrical connections between the cartridge and the housing such as via piezoelectric or radio frequency atomization. Alternatively, the power source may be positioned in the cartridge such that electrical connection with connector is not required.

In use, when a user draws on the aerosol delivery device 100, the heating element 240 of the atomizer 212 is activated to vaporize components of the aerosol precursor composition. Drawing upon the mouthpiece 220 of the aerosol delivery device causes ambient air to enter and pass through an opening in the connector 106 or in the cartridge 200. In the cartridge, the drawn air combines with the formed vapor to form an aerosol. The aerosol is whisked, aspirated or otherwise drawn away from the heating element and out the opening in the mouthpiece of the aerosol delivery device. However, the flow of air may be received through other parts of the aerosol delivery device in other implementations. As noted above, in some implementations the cartridge may include the flow tube 210. The flow tube may be configured to direct the flow of air to the heating element.

In particular, a sensor in the aerosol delivery device 100 may detect the flow of air throughout the aerosol delivery device. When a flow of air is detected, the control component 108 may direct current to the heating element 240 through a circuit including the first heating terminal 234a and the second heating terminal 234b. Accordingly, the heating element may vaporize the aerosol precursor composition directed to an aerosolization zone from the reservoir 214 by the liquid transport element 238. Thus, the mouthpiece 220 may allow passage of aerosol (i.e., the components of the aerosol precursor composition in an inhalable form) therethrough to a consumer drawing thereon.

FIG. 4 illustrates a perspective view of the aerosol delivery device 100 in the closed configuration, and FIG. 5 illustrates a perspective view of the aerosol delivery device in the extended configuration, having a particular form factor according to some example implementations. As illustrated, the housing 102 may define an ergonomic shape configured to comfortably fit within a user's hand. The shape of the housing, however, is not limited and may be any shape that accommodates the various elements as described herein. In some implementations, the housing may be expressly non-cylindrical.

As further illustrated in FIG. 5, the aerosol delivery device 100 may additionally include an attachment mechanism 112. The attachment mechanism 112 may comprise a loop, a clip, a ring, or other mechanism configured to attach to another device such as a keychain, a carabineer, or a lanyard. Accordingly, the aerosol delivery device may be retained in a desired position. Thus, for example, a user may be able to more easily secure the aerosol delivery device in a desired position at which the aerosol delivery device may be less prone to damage or misplacement.

The aerosol delivery device 100 may additionally include an input mechanism 114. The input mechanism may comprise a pushbutton or other switch configured to receive an input from a user. When the input mechanism is actuated, the aerosol delivery device may produce an output corresponding to a status of the aerosol delivery device. For example, the aerosol delivery device may output sound, vibration, or light. As illustrated in FIG. 4, the aerosol delivery device may further comprise an indicator 116. The indicator may comprise a light transmitter (e.g., plastic or glass, which may be tinted a desired color). Further, the indicator may include a light emitter, which may comprise an incandescent bulb or light emitting diode (LED). Thereby, the light emitter may illuminate the light transmitter, which may direct the light outwardly therethrough to output a status of the aerosol delivery device.

The indicator 116 may flash or otherwise illuminate to indicate a remaining or used portion of the capacity of the power source 104 or the reservoir 214. For example, a relatively large number of flashes of the indicator upon actuation of the input mechanism 114 may correspond to a relatively large remaining capacity of the power source or the reservoir. Conversely, a relatively small number of flashes of the indicator upon actuation of the input mechanism may correspond to a relatively small remaining capacity of the power source or the reservoir. However, the indicator and/or other output mechanisms may be employed to output various other information and/or output information in various other manners. Examples of other information that may be outputted include error messages, operational modes, historical usage information, etc.

In some implementations, the aerosol delivery device 100 may include a display 118, as illustrated in FIGS. 4 and 5. The display may be provided in addition to, or as an alternate for, the indicator 116. The display may be configured to output various information including information regarding a status of the aerosol delivery device, information unrelated to the status of the aerosol delivery device (e.g., the present time), and/or non-informative graphics (e.g., graphics provided for user entertainment purposes). Thereby, the display may be configured to output any or all of the information described above (e.g., a remaining or used portion of the capacity of the power source 104 or the reservoir 214) in any form such as graphical form and/or a numerical form. Further, in some implementations operation or the display may be controlled by the input mechanism 114 or a separate input mechanism. The display, for example, may be a touchscreen and thus may be configured for user input. In some implementations, the display may provide icons, menus, or the like configured to allow a user to make control selections related to the functioning of the aerosol delivery device, check a specific status of the device, or the like. Although the display is illustrated as encompassing only a relatively small portion of the aerosol delivery device, it is understood that the display may cover a significantly greater portion of the aerosol delivery device.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the flow sensor or another sensor or detector for control of supply of electric power to the heating element 240 when aerosol generation is desired (e.g., upon draw during use). As such, for example, there is provided a manner or method of turning off the power supply to the heating element when the aerosol delivery device is not be drawn upon during use, and for turning on the power supply to actuate or trigger the generation of heat by the heating element during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 108 or another control mechanism for controlling the amount of electric power to the heating element 240 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., U.S. Pat. App. Pub. No. 2014/0261408 to DePiano et al., and U.S. patent application Ser. No. 14/286,552 to Brinkley et al., all of which are incorporated herein by reference in their entireties.

FIG. 6 illustrates a more particular configuration of electronic components 600 that may be utilized within a suitable aerosol delivery device such as aerosol delivery device 100, according to some example implementations. The aerosol delivery device may be configured to execute computer code for performing the operations described herein. As illustrated, the aerosol delivery device may comprise a processor 602 (e.g., control component 108) that may be a microprocessor for controlling the overall operation thereof. In one implementation the processor 602 may be particularly configured to execute program code instructions related to the functions described herein, including the operations for assembling the aerosol delivery devices or portions thereof of the present disclosure. The aerosol delivery device may also include a memory device 604. The memory device 604 may include non-transitory and tangible memory that may be, for example, volatile and/or non-volatile memory. The memory device 604 may be configured to store information, data, files, applications, instructions or the like. For example, the memory device 604 could be configured to buffer input data for processing by the processor 602. Additionally or alternatively, the memory device 604 may be configured to store instructions for execution by the processor 602.

The aerosol delivery device 600 may also include a user interface 606 that allows a user to interact therewith. For example, the user interface 606 can include a user input interface (e.g., input mechanism 114) that can take a variety of forms, such as a pushbutton, keypad, dial, touch screen, audio input interface, visual/image capture input interface, input in the form of sensor data, etc. Still further, the user interface 606 may include a user output interface such as a display (e.g., display 118), speaker, or other output device configured to output information to the user.

The aerosol delivery device 600 may further include a communication interface 608 configured to enable wireless communication. In some examples, the communication interface may be included on a PCB of the control component, or a separate PCB that may be coupled to the PCB or one or more components of the control component. The communication interface may enable the aerosol delivery device to wirelessly communicate with one or more networks, computing devices or other appropriately-enabled devices. Examples of suitable computing devices include any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. And in yet another example, the computing device may be embodied as an electric beacon such as one employing iBeacon™ technology developed by Apple Inc. Examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2016, to Henry, Jr. et al., each of which is incorporated herein by reference in its entirety.

The communication interface 608 may include, for example, an antenna (or multiple antennas) and supporting hardware and/or software for enabling wireless communication with a communication network (e.g., a cellular network, Wi-Fi, WLAN, and/or the like), and/or for supporting device-to-device, short-range communication, in accordance with a desired communication technology. Examples of suitable short-range communication technologies that may be supported by the communication interface include various near field communication (NFC) technologies, wireless personal area network (WPAN) technologies and the like. More particular examples of suitable WPAN technologies include those specified by IEEE 802.15 standards or otherwise, including Bluetooth, Bluetooth low energy (Bluetooth LE), ZigBee, infrared (e.g., IrDA), radio-frequency identification (RFID), Wireless USB and the like. Yet other examples of suitable short-range communication technologies include Wi-Fi Direct, as well as certain other technologies based on or specified by IEEE 802.11 and/or IEEE 802.15.4 standards and that support direct device-to-device communication.

According to example implementations of the present disclosure, the input mechanism 114, such as a pushbutton, and the display 118 may provide a user interface for the aerosol delivery device 100. The control component 108 may be contained within the 102 housing, coupled to the user interface and configured to control operation of at least one functional element of the aerosol delivery device 100. FIGS. 7-15 illustrate various functions of such a user interface, according to some example implementations.

As illustrated in FIG. 7, in some example implementations, the control component 108 may be configured to control the display 118 to present a menu including a plurality of menu items 700. In some example implementations, due to the limited surface area provided by a typically small form-factor of the aerosol delivery device 100, the plurality of menu items may be selectable using only a single pushbutton (e.g., input mechanism 114) of the aerosol delivery device 100, which in some examples implementations may only include the single pushbutton. The control component may be configured to navigate the plurality of menu items, and select a currently-presented menu item of the plurality of menu items for control of the respective functional element, in response to respective first and second types of presses of the pushbutton in which the first and second types of presses are of different durations.

In some example implementations, the duration of the second type of press of the pushbutton is substantially longer than the duration of the first type of press of the pushbutton. In such implementations, in addition to selecting the currently-presented menu item, the control component 108 may be configured to control the display 118 to present a progress bar 702 associated with the currently-presented menu item. The progress bar may visually indicate progression of a press of the pushbutton up to the duration of the second type of press of the pushbutton. In some implementations, the control component may be configured to automatically update the progress bar with progression of the press of the pushbutton, and reset the progress bar in at least one instance in which the pushbutton is released before the duration of the second type of press.

In some example implementations, as illustrated in FIGS. 7 and 8, the display 118 may enter a standby mode 800 after a predetermined period of time has elapsed without a press of the pushbutton of either the first type or second type which may be simply referred to herein as an "idle duration." In such an implementation, the control component 108 may be configured to turn off the display after the idle duration (e.g., three (3) second duration in which without a press of the pushbutton of either the first type or second type). It should be noted that, although many of the example implementations discuss the idle duration with reference to a three (3) second period of time, a duration of time may be greater than or less than three (3) seconds.

Each menu item of the plurality of menu items may be associated with a respective functional element of the aerosol delivery device. The menu items may include, for example, a status menu 900, a heating element power setting menu 1000, a stealth mode menu 1100, Bluetooth menu 1200, and/or a power menu 1300.

Figure 7:
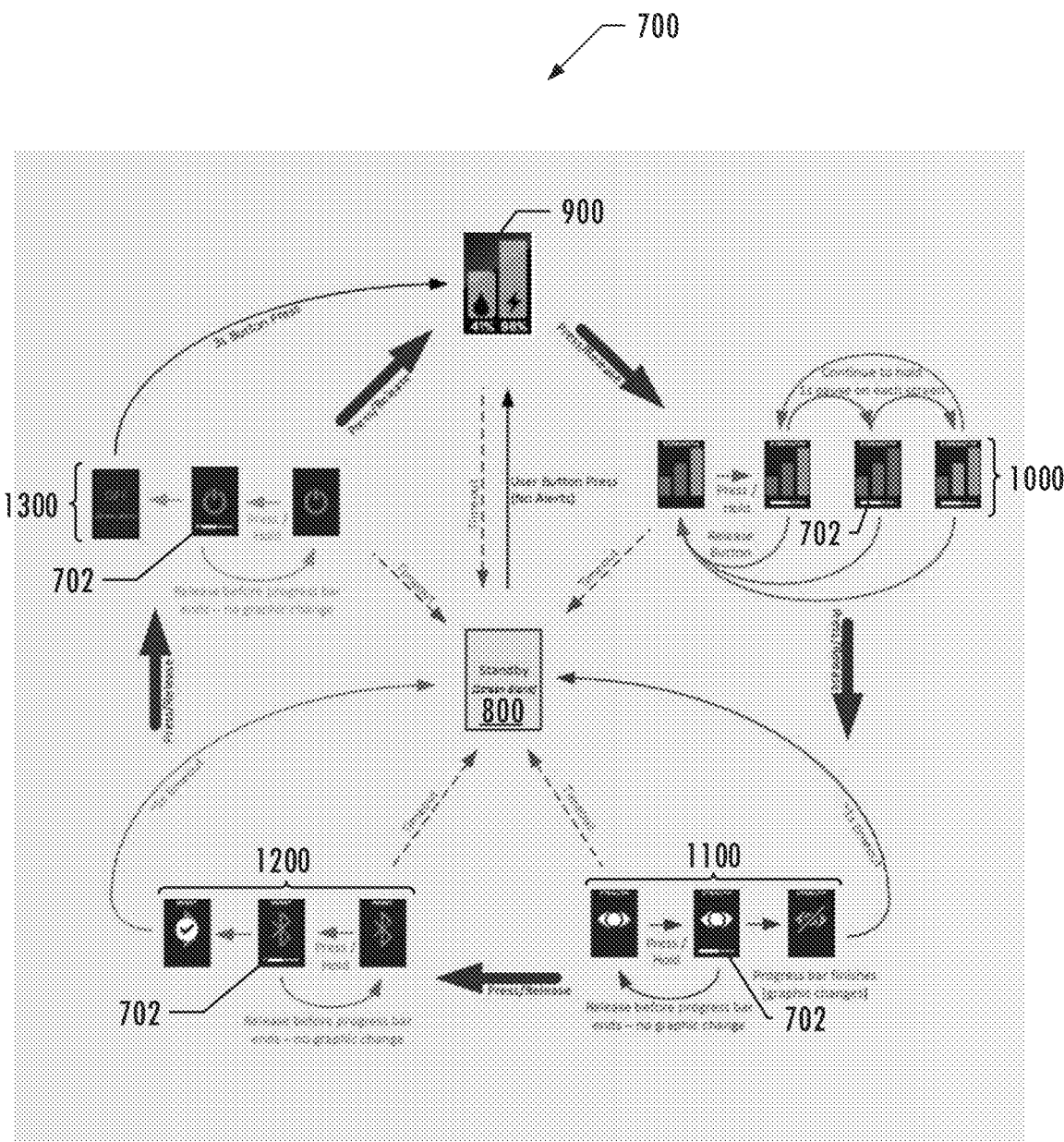
Figure 8:
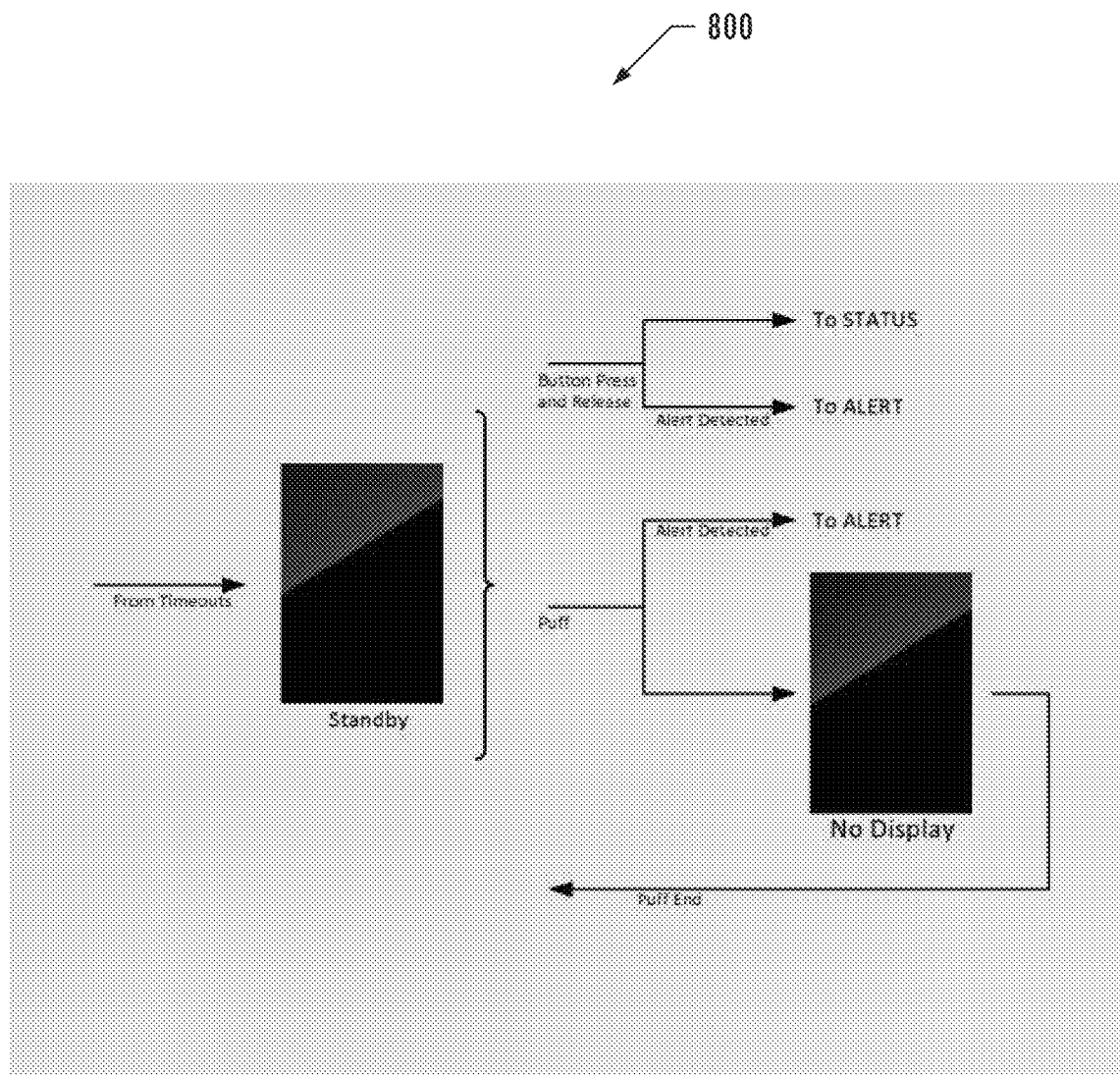
Figure 9:
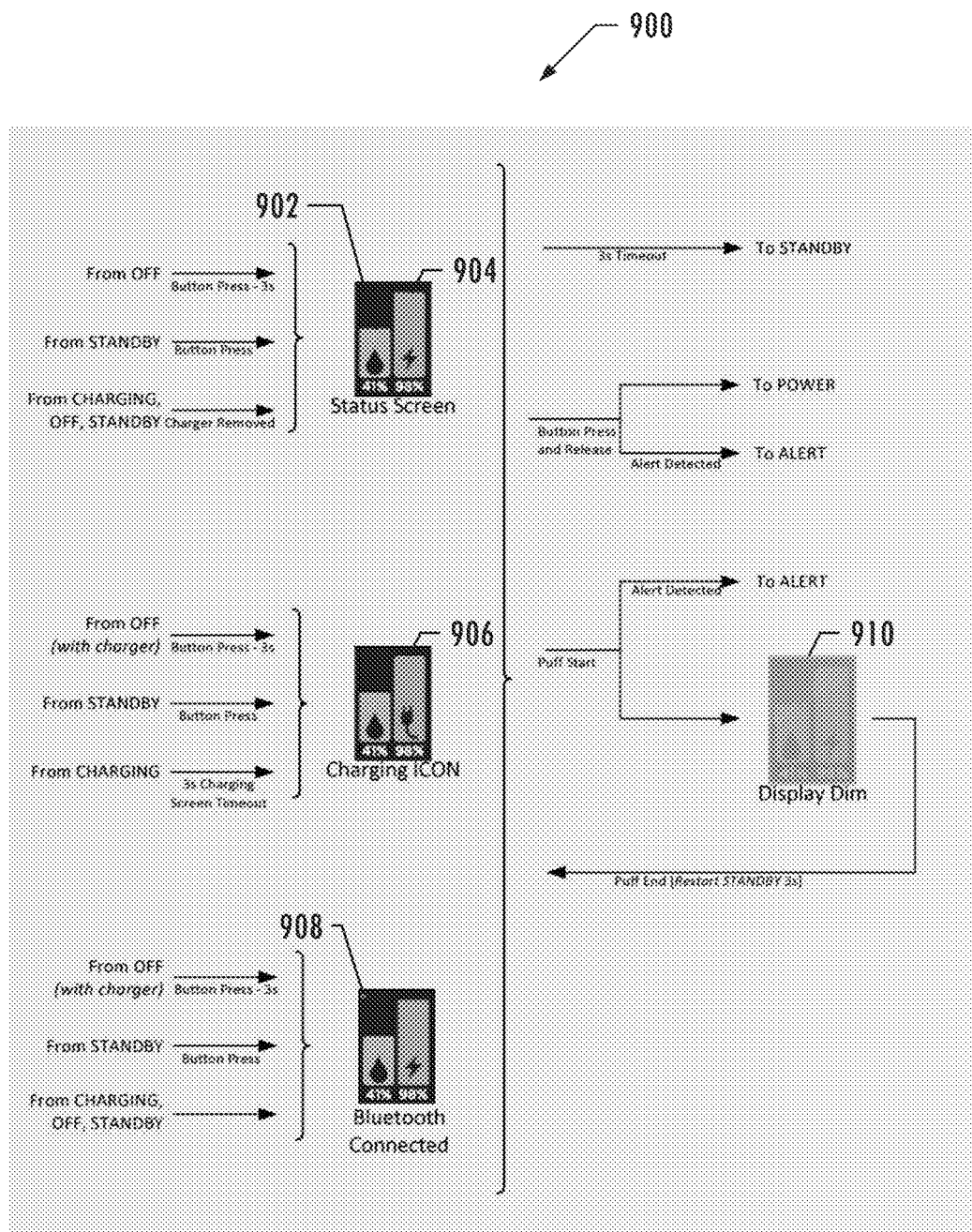

In some example implementations, in at least one instance, the respective functional element with which the currently-presented menu item is associated is the power source 104, and the cartridge 200 containing an aerosol precursor composition. In such implementations and instance(s), the control component 108 may be configured to control the display 118 to present the status menu 900, as illustrated in FIGS. 7 and 9. The status menu may indicate a current power level of the power source and a current level of the aerosol precursor composition within the cartridge (e.g., a remaining or used portion of the capacity of the power source or the reservoir 214).

The status menu 900 may present graphical icons that indicate the current status of the aerosol delivery device 100. The graphical icons may include, for example, a reservoir capacity icon 902, a power capacity icon 904, a charging icon 906, and a Bluetooth indicator 908. The reservoir capacity icon may indicate a percentage of remaining aerosol precursor composition within the reservoir 214, the power capacity icon may indicate the remaining the remaining portion of the capacity of the power source portion of the capacity of the power source 104, the charging icon may similarly indicate the remaining portion of the capacity of the power source and further indicate that the aerosol delivery device is connected to a charger, and the Bluetooth indicator may indicate that the aerosol delivery device is currently connected with a Bluetooth compatible device. In some example implementations, the graphical icon immediately transitions from the power capacity icon to the charging icon, or vice versa, in response to the charger being connected or disconnected from the aerosol delivery device.

In some example implementations, the status menu 900 may be initially presented if the display 118 was previously turned off or in standby mode 800, or the aerosol delivery device 100 is alternating states of charging (e.g., connecting to, or being disconnected from a charger). In one implementation, for example, a short or long button-press (e.g., a second type of press of three (3) second duration) may transition the display from being turned off to presenting the status screen. Further a three (3) second idle duration after presentation of the status screen may cause the display to reenter standby mode. In some implementations, a single button press of the first type may cause the display to transition from the status screen to a subsequent menu item or to present an alert. Similarly, a detection of airflow throughout the aerosol delivery device may cause the display to dim 910 while presenting the status screen or to present an alert.

Figure 10:
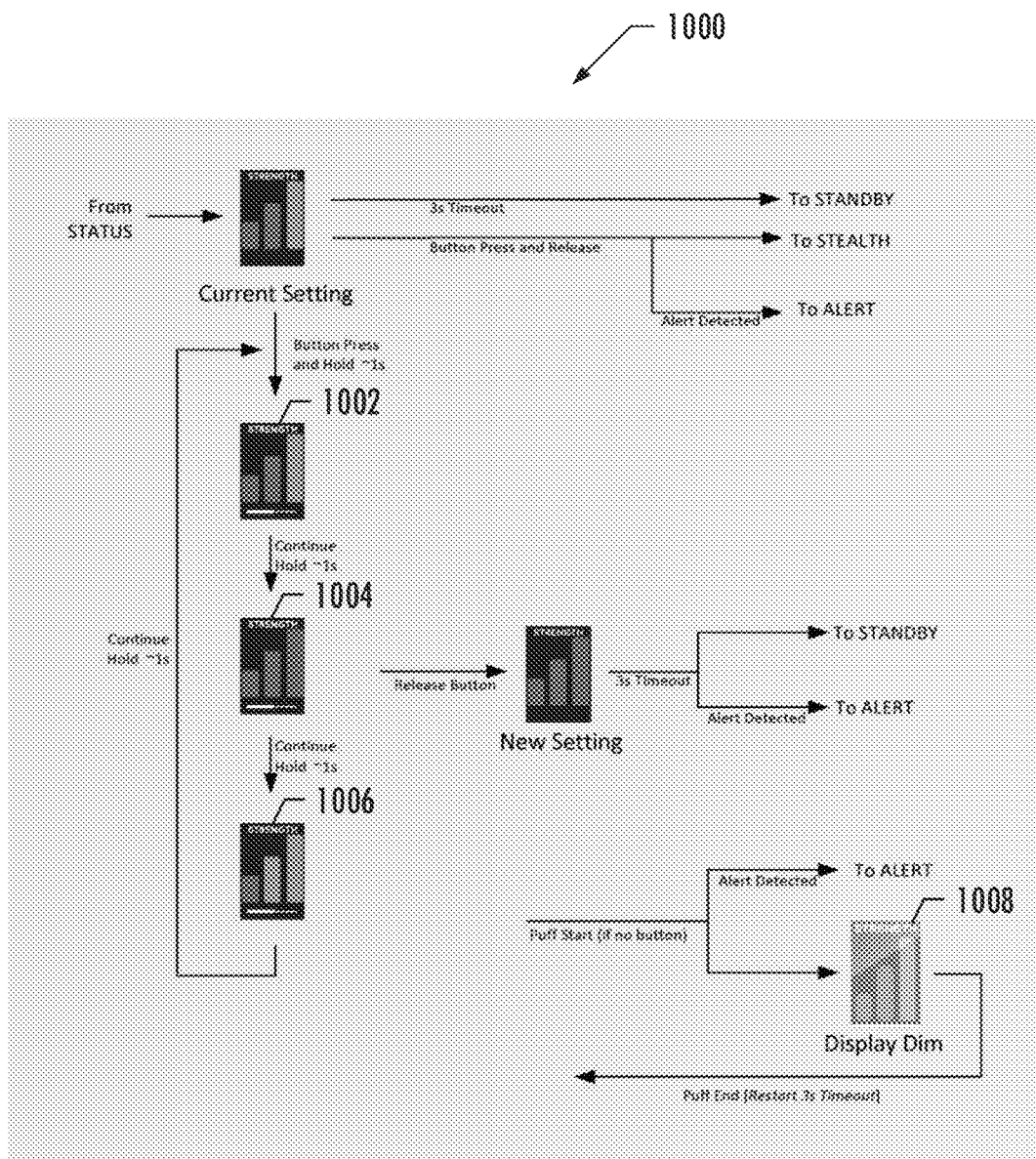

In some example implementations, in at least one instance, the respective functional element with which the currently-presented menu item is associated is the heating element 240. In such implementations and instance(s), the control component 108 may be configured to control the display 118 to present the heating element power setting menu 1000, as illustrated in FIGS. 7 and 10. In response to the selection of the heating element power setting menu item, the control component may effect an alteration of the power level of the heating element, and control the display to present a confirmation of the alteration.

In some example implementations, the power level of the heating element 240 may be altered from a current power setting 1002 to a second setting 1004, or third setting 1006 in response to a second type press of the pushbutton. For example, the power level may be altered from low, normal, or high heating element power levels. The heating element power setting menu items may continuously transition as the duration increases and the progress bar may subsequently update. Upon release of the pushbutton, the control component 108 may effect alteration of the power level of the heating element according to the currently-presented menu item.

In some example implementations, the control component 108 may control the display 118 to present the plurality of menu items upon user control of the aerosol delivery device 100 via an external device (e.g., a Bluetooth wireless link). In at least one instance, the control component may thereby effect alteration of the power level of the heating element via the external device according to a corresponding menu item of the currently-presented menu item. For example, the user may visualize a currently-presented menu item (e.g., power setting items) via a mobile application and navigate menu items at the external device that correspond to the plurality or menu items such that the control component may simultaneously update the currently-presented menu item to reflect a corresponding menu item being presented on a display of the external device, upon user progression to the corresponding menu item at the external device.

In one implementation, for example, a three (3) second idle duration after presentation of the heating element power setting menu 1000 may cause the display 118 to reenter standby mode 800. In some implementations, a single button press of the first type may cause the display to transition from the heating element power setting menu to a subsequent menu item or to present an alert. Similarly, a detection of airflow throughout the aerosol delivery device 100 may cause the display to dim 1008 while presenting the status screen or to present an alert.

Figure 11:
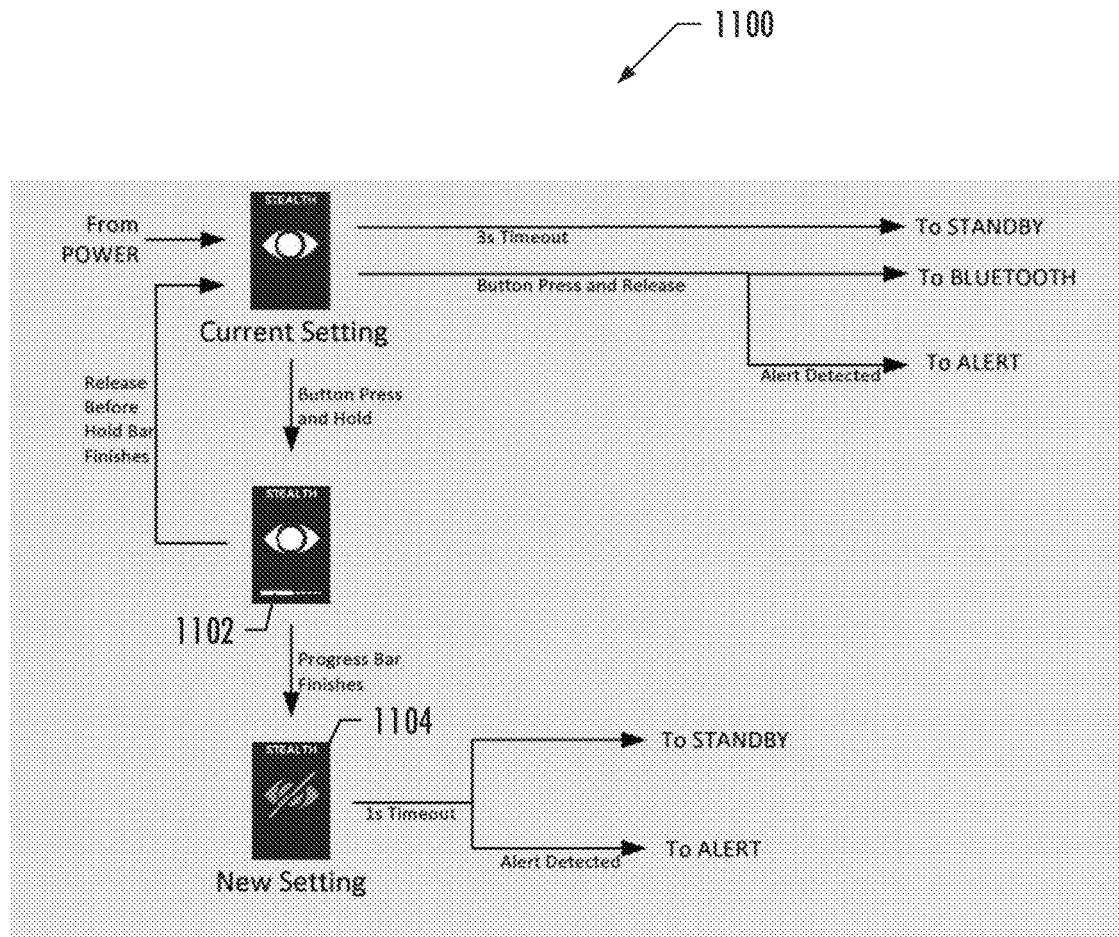

In some example implementations, in at least one instance, the respective functional element with which the currently-presented menu item is associated is the display 118, and the presently-presented menu item is further associated with an audio component. In such implementations and instance(s), the control component 108 may be configured to control the display to present the stealth mode menu 1100, as illustrated in FIGS. 7 and 11. In response to the selection of the stealth mode menu item, the control component may effect a dimming of the display and a muting of the audio component. The progress bar 1102 may automatically updated with progression of the press of the pushbutton, and upon completion, the control component may further control the display to present a confirmation 1104 of the dimming and muting.

In one implementation, for example, a three (3) second idle duration after presentation of the stealth mode menu 1100 may cause the display 118 to enter standby mode 800. In some implementations, a single button press of the first type may cause the display to transition from the stealth mode menu to a subsequent menu item or to present an alert. Similarly, a one (1) second idle duration after confirmation 1104 of the dimming and muting may cause the display to enter standby mode or to present an alert.

Figure 12:
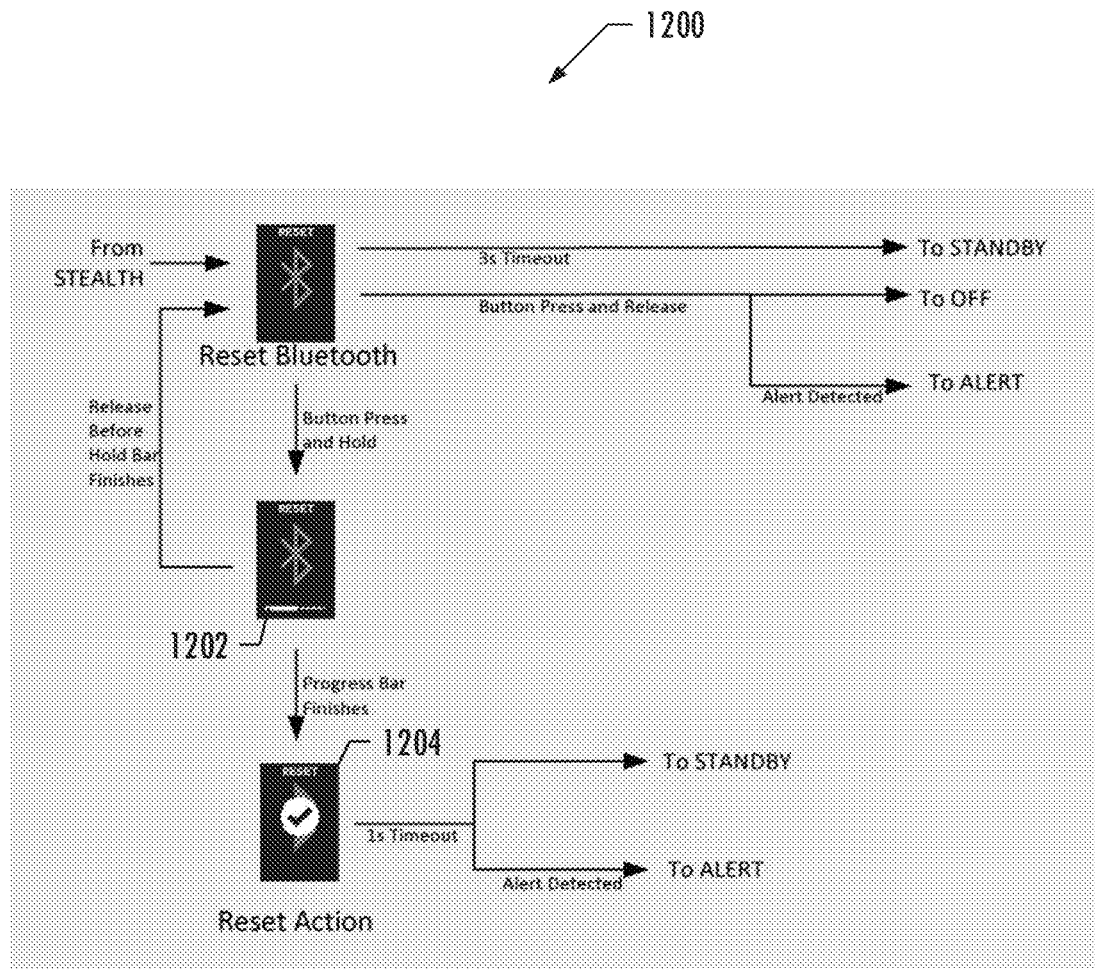

In some example implementations, in at least one instance, the respective functional element with which the currently-presented menu item is associated is a Bluetooth communication interface (e.g., communication interface 608). It should be noted however, that while these example implementations may be discussed in the context of a Bluetooth communication interface, the currently-presented menu item may associated with other communication interfaces not expressly stated herein. In such implementations and instance(s), the control component 108 may be configured to control the display 118 to present the Bluetooth menu 1200, as illustrated in FIGS. 7 and 12. In response to the selection of the Bluetooth menu item, the control component may effect a reset of the Bluetooth communication interface. The progress bar 1202 may automatically updated with progression of the press of the pushbutton, and upon completion, the control component may further control the display to present a confirmation 1204 of the reset.

In one implementation, for example, a three (3) second idle duration after presentation of the Bluetooth menu 1200 may cause the display 118 to enter standby mode 800. In some implementations, a single button press of the first type may cause the display to transition from a currently-presented menu to a subsequent menu item or to present an alert. Similarly, a one (1) second idle duration after confirmation 1204 of the reset may cause the display to enter standby mode or to present an alert.

Figure 13:
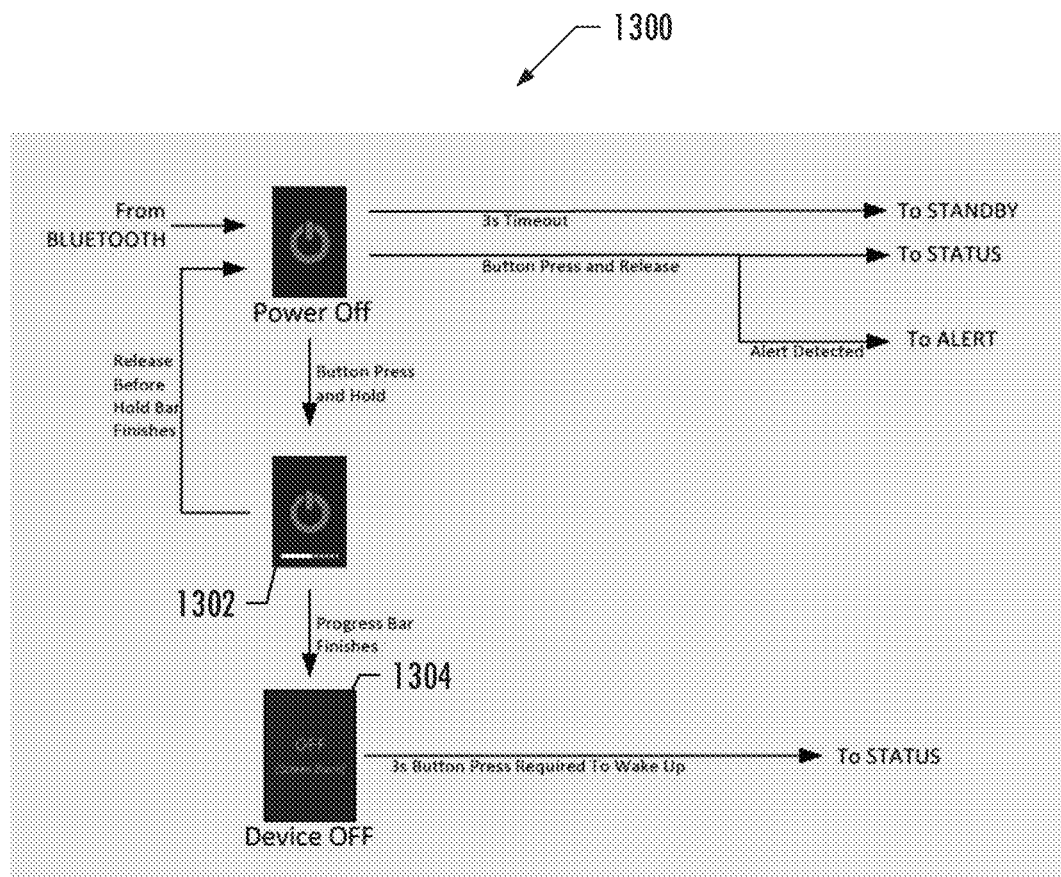
Figure 14:
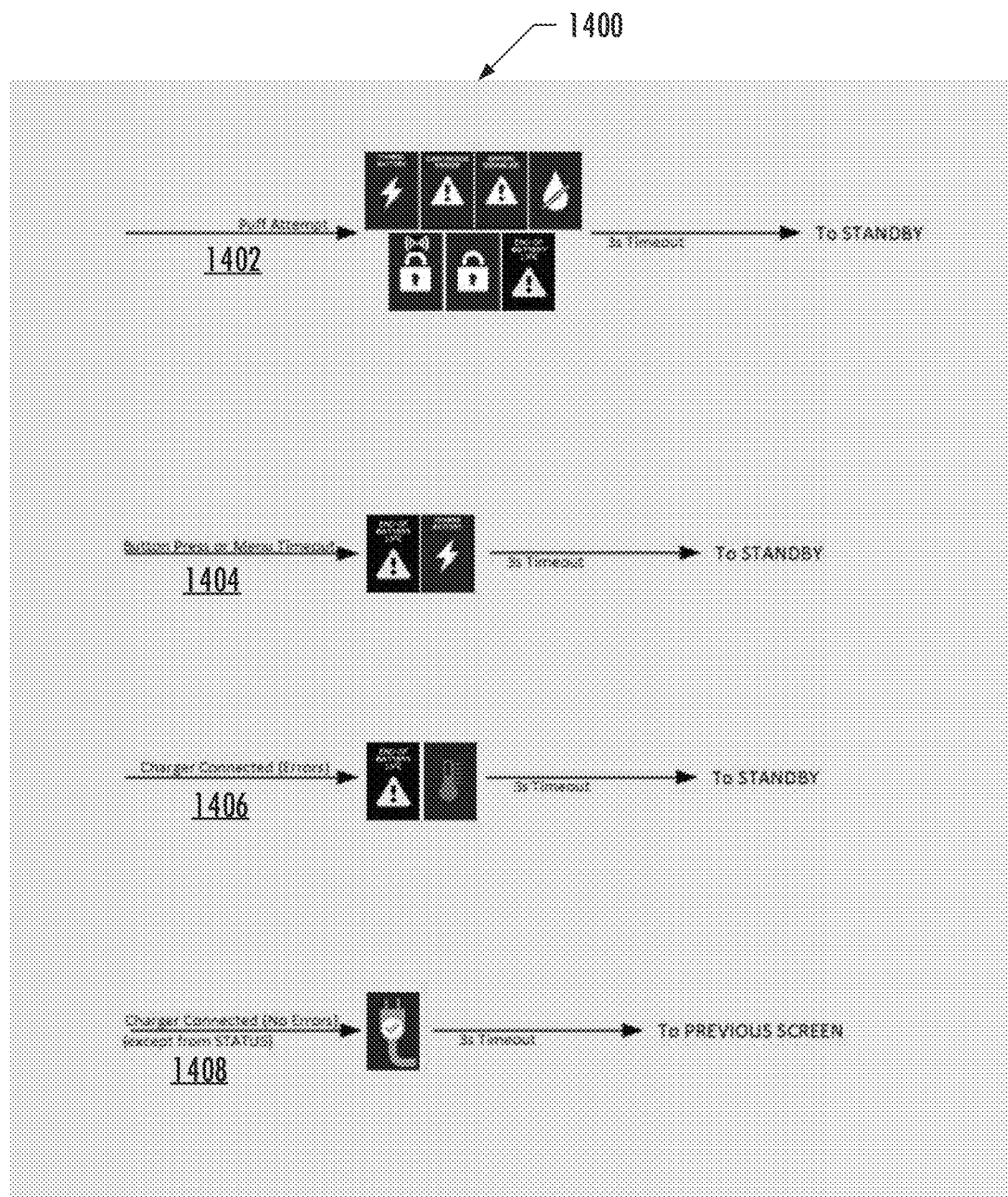

In some example implementations, in at least one instance, the respective functional element with which the currently-presented menu item is associated is a power source 104 of the aerosol delivery device. In such implementations and instance(s), the control component 108 may be configured to control the display 118 to present the power menu 1300, as illustrated in FIGS. 7 and 13. In response to the selection of the power menu item, the control component may cause the aerosol delivery device to power off. The progress bar 1302 may automatically updated with progression of the press of the pushbutton, and upon completion, the control component may further control the aerosol delivery device and subsequently the display to turn off 1304.

In one implementation, for example, a three (3) second idle duration after presentation of the power menu 1300 may cause the display 118 to enter standby mode 800. In some implementations, a single button press of the first type may cause the display to transition from the Bluetooth menu to a subsequent menu item or to present an alert. Similarly, a three (3) second duration of the second type of press while the aerosol delivery device is currently off, may cause the device to be powered on.

In some example implementations, the control component 108 may be configured to detect an alert event associated with the aerosol delivery device 100, and in response to a separate display trigger, control the display 118 to present an alert 1400 corresponding thereto. The separate display trigger may include, for example, at least one of the detection of airflow through at least a portion of the at least one housing 1402, first and second types of presses of the pushbutton or idle duration 1404, and the connection of the aerosol delivery device to a charging component 1406, 1408 respectively. After presentation of an alert the display may enter standby mode 800 or present the previously-presented menu item. The alerts may include, for example, a cartridge error, end of power source capacity alert, charge power source alert, empty cartridge alert, charging power source alert, identification alert, Bluetooth bond confirmation alert, safety issue alert, locked display alerts, unlocked display alert, battery temperature alert, and the like. In some example, implementations, as illustrated in FIG. 15, one or more of the menu items or alerts may be presented on the display in response to an interaction between the aerosol delivery device and an application associated with an external device.

FIG. 16 illustrates a flowchart including various operations of a method 1600 for controlling operation of an aerosol delivery device, in accordance with an example implementation of the present disclosure. The aerosol delivery device includes at least one housing containing a user interface including a pushbutton and a display on the at least one housing, and a control component contained within the at least one housing and coupled to the user interface. As shown at block 1602, the method may include, at the control component, controlling operation of at least one functional element of the aerosol delivery device in response to detection of airflow through at least a portion of the at least one housing. The method may include controlling the display to present a menu including a plurality of menu items selectable using only the pushbutton, as shown at block 1604. Each menu item of the plurality of menu items may be associated with a respective functional element of the aerosol delivery device. The method may also include navigating the plurality of menu items, and selecting a currently-presented menu item of the plurality of menu items for control of the respective functional element, in response to respective first and second types of presses of the pushbutton, as shown at block 1606. The first and second types of presses may be of different durations.

The various aspects, implementations, implementations or features of the described implementations can be used separately or in any combination. Various aspects of the described implementations can be implemented by software, hardware or a combination of hardware and software. The described implementations can also be embodied as computer readable code on a computer readable medium for controlling the above-described operations. In particular, computer readable code may be configured to perform each of the operations of the methods described herein and embodied as computer readable code on a computer readable medium for controlling the above-described operations. In this regard, a computer readable storage medium, as used herein, refers to a non-transitory, physical storage medium (e.g., a volatile or non-volatile memory device, which can be read by a computer system. Examples of the computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

As noted above, the aerosol delivery device 100 may be configured to execute computer code for performing the above-described operations. In this regard, an implementation of a non-transitory computer readable medium for storing computer instructions executed by a processor in the aerosol delivery device is provided. The non-transitory computer readable medium may comprise program code instructions for controlling an aerosol delivery device and user interface discussed herein.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-15 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
at least one housing;
a plurality of functional elements, the plurality of functional elements including at least:
a communication interface configured to enable wireless communication with an external device; and
an atomizer; and
a control component contained within the at least one housing and coupled to the communication interface, the control component being configured to control operation of at least the atomizer in response to detection of airflow through at least a portion of the at least one housing;
wherein the control component is configured to communicate with the external device that is configured to present a plurality of menu items selectable at the external device, and
wherein, in response to receiving a signal from the external device indicating navigation of the plurality of menu items, the control component is configured to control one of the plurality of functional elements or provide an indication of a status of at least one of the plurality of functional elements for display on the external device.

2. The aerosol delivery device of claim 1, wherein the plurality of functional elements further includes a power source of the aerosol delivery device and the plurality of menu items includes a menu item, which, when selected causes a power off signal to be sent to the control component, wherein, in response to the control component receiving the power off signal, the control component is configured to deactivate the power source and thereby cause the aerosol delivery device to power off.

3. The aerosol delivery device of claim 1, wherein the plurality of menu items includes a menu item, which, when selected causes a power alteration signal to be sent to the control component, wherein, in response to the control component receiving the power alteration signal, the control component is configured to effect an alteration of a power level of the atomizer.

4. The aerosol delivery device of claim 1, wherein the communication interface is a Bluetooth communication interface, and
wherein the plurality of menu items includes a menu item, which, when selected causes a reset signal to be sent to the control component, wherein, in response to receiving the reset signal, the control component is configured to effect a reset of the Bluetooth communication interface.

5. The aerosol delivery device of claim 1, wherein the plurality of functional elements further includes a user output interface component, and wherein the plurality of menu items includes a menu item, which, when selected causes an output modification signal to be sent to the control component, wherein, in response to receiving the output modification signal, the control component is configured to modify an output characteristic of the user output interface component.

6. The aerosol delivery device of claim 1, wherein the plurality of functional elements further includes a power source of the aerosol delivery device, and wherein the control component is configured to send a current power level status of the power source to the external device for display.

7. The aerosol delivery device of claim 1, wherein the control component is configured to send a status of aerosol precursor composition contained by the aerosol delivery device to the external device for display.

8. The aerosol delivery device of claim 1, wherein the control component is further configured to detect an alert event associated with the aerosol delivery device and send an indication of the alert event to the external device.

9. The aerosol delivery device of claim 8, wherein the alert event comprises one of a cartridge error, end of power source capacity alert, charge power source alert, empty cartridge alert, charging power source alert, identification alert, Bluetooth bond confirmation alert, safety issue alert, locked display alerts, unlocked display alert, and battery temperature alert.

10. The aerosol delivery device of claim 1, wherein the plurality of menu items includes at least one of a status menu, a heating element power setting menu, a stealth mode menu, a Bluetooth menu, or a power menu.

11. A method for controlling operation of an aerosol delivery device including at least one housing, a plurality of functional elements, the plurality of functional elements including at least a communication interface configured to enable wireless communication with an external device and an atomizer, the aerosol delivery device further comprising a control component contained within the at least one housing and coupled to the communication interface, the method comprising, at the control component:
controlling operation of at least the atomizer in response to detection of airflow through at least a portion of the at least one housing;
communicating with the external device that presents a plurality of menu items selectable at the external device;
receiving a signal from the external device indicating navigation of the plurality of menu items; and
in response to receiving the signal, either or both of controlling one of the plurality of functional elements, or providing an indication of a status of at least one of the plurality of functional elements for display on the external device.

12. The method of claim 11, wherein the plurality of functional elements further includes a power source of the aerosol delivery device and the plurality of menu items includes a menu item, which, when selected causes a power off signal to be transmitted to the control component, the method further comprising, at the control component:

in response to the control component receiving the power off signal, controlling the power source to deactivate, thereby causing the aerosol delivery device to power off.

13. The method of claim 11, wherein the plurality of menu items includes a menu item, which, when selected causes a power alteration signal to be sent to the control component, the method further comprising, at the control component:
in response to the control component receiving the power alteration signal, causing an alteration of a power level of the atomizer.

14. The method of claim 11, wherein the communication interface is a Bluetooth communication interface, and
wherein the plurality of menu items includes a menu item, which, when selected causes a reset signal to be sent to the control component, the method further comprising, at the control component:
in response to the control component receiving the reset signal, causing a reset of the Bluetooth communication interface.

15. The method of claim 11, wherein the plurality of functional elements further includes a user output interface component, and wherein the plurality of menu items includes a menu item, which, when selected causes an output modification signal to be sent to the control component, wherein the method further comprises, at the control component:
in response to the control component receiving the output modification signal, causing a modification to an output characteristic of the user output interface component.

16. The method of claim 11, wherein the plurality of functional elements further includes a power source of the aerosol delivery device, and wherein the method further comprises, at the control component, providing a current power level status of the power source for display on the external device.

17. The method of claim 11, wherein the method further comprises, at the control component, communicating a status of aerosol precursor composition contained by the aerosol delivery device to the external device for display.

18. The method of claim 11, wherein the method further comprises, at the control component:
detecting an alert event associated with the aerosol delivery device; and
sending an indication of the alert event to the external device.

19. The method of claim 18, wherein the alert event comprises one of a cartridge error, end of power source capacity alert, charge power source alert, empty cartridge alert, charging power source alert, identification alert, Bluetooth bond confirmation alert, safety issue alert, locked display alerts, unlocked display alert, and battery temperature alert.

20. The method of claim 11, wherein the plurality of menu items includes at least one of a status menu, a heating element power setting menu, a stealth mode menu, a Bluetooth menu, or a power menu.

* * * * *